(12) United States Patent  (10) Patent No.: US 6,740,084 B2
Ryan  (45) Date of Patent: May 25, 2004

(54) METHOD AND DEVICE TO ENHANCE RF ELECTRODE PERFORMANCE

(75) Inventor: Thomas P. Ryan, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 66 days.

(21) Appl. No.: 10/022,925

(22) Filed: Dec. 18, 2001

(65) Prior Publication Data

US 2003/0114849 A1 Jun. 19, 2003

(51) Int. Cl.⁷ ................................................ A61B 18/18
(52) U.S. Cl. ........................ 606/41; 606/50; 607/101
(58) Field of Search ................ 606/41, 42, 48–50; 607/101, 102, 116

(56) References Cited

U.S. PATENT DOCUMENTS

| 4,532,924 | A | * | 8/1985 | Auth et al. | 606/50 |
| 4,682,596 | A | * | 7/1987 | Bales et al. | 606/39 |
| 5,582,609 | A | * | 12/1996 | Swanson et al. | 606/39 |
| 5,743,903 | A | | 4/1998 | Stern et al. | |
| 5,954,719 | A | | 9/1999 | Chen et al. | |
| 6,066,139 | A | | 5/2000 | Ryan et al. | |
| 6,106,522 | A | * | 8/2000 | Fleischman et al. | 606/41 |
| 6,447,506 | B1 | * | 9/2002 | Swanson et al. | 606/41 |

FOREIGN PATENT DOCUMENTS

| DE | 19739699 | 3/1999 |
| WO | 0036985 | 6/2000 |

* cited by examiner

Primary Examiner—Michael Peffley

(57) ABSTRACT

A bipolar electrode instrument is provided for use in the performance of RF ablation electrosurgery. The bipolar electrode instrument includes an elongated catheter for insertion into an affected tissue to be treated within a patient and at least one pair of spaced-apart bipolar electrode members, each of the electrode members being connected to the catheter. An RF energy source and a plurality of electrical lines are included for applying voltage to each of the electrode members. Mechanisms are included for regulating the amount of heat generated by each of the electrode members when voltage is applied thereto.

17 Claims, 7 Drawing Sheets

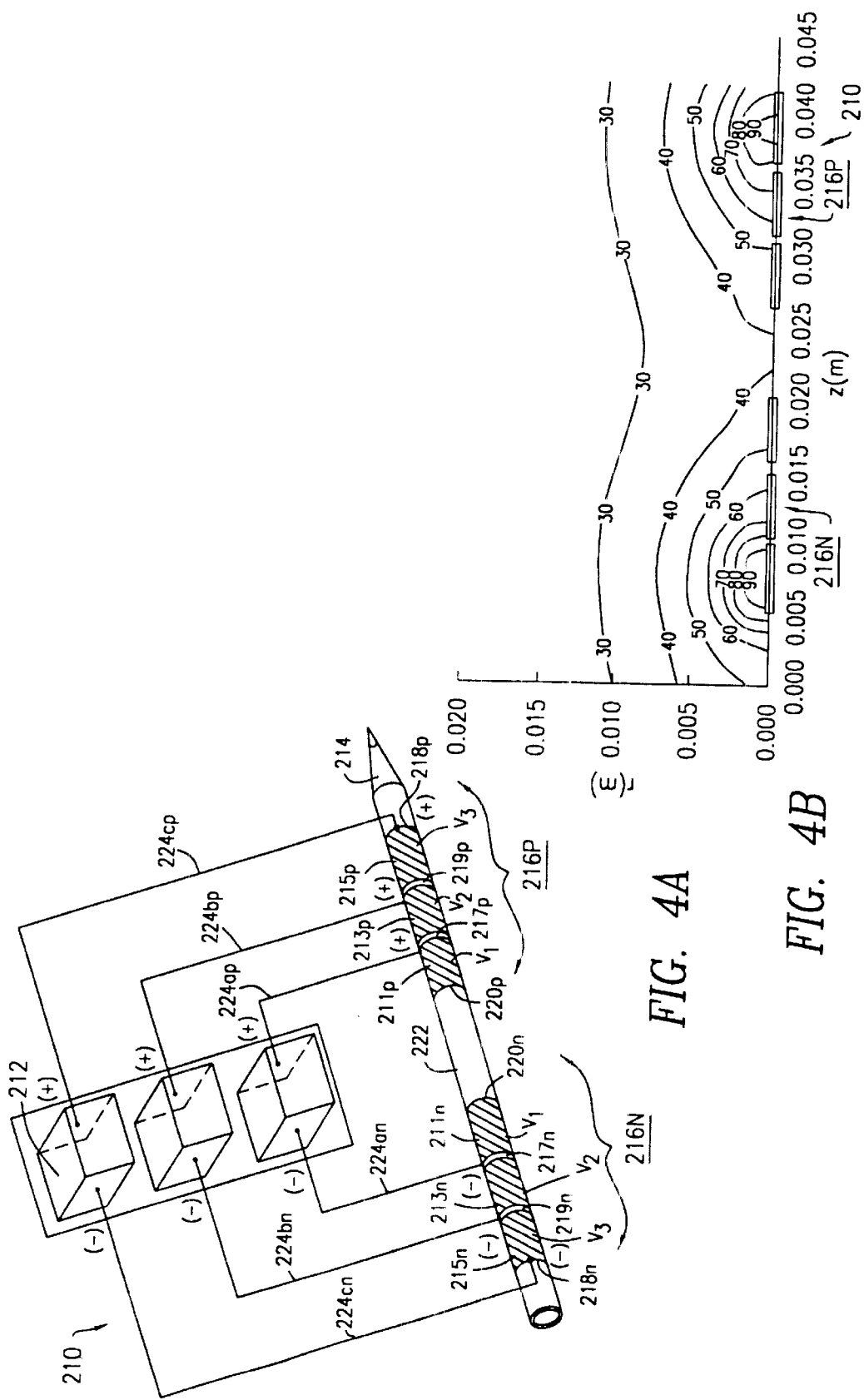

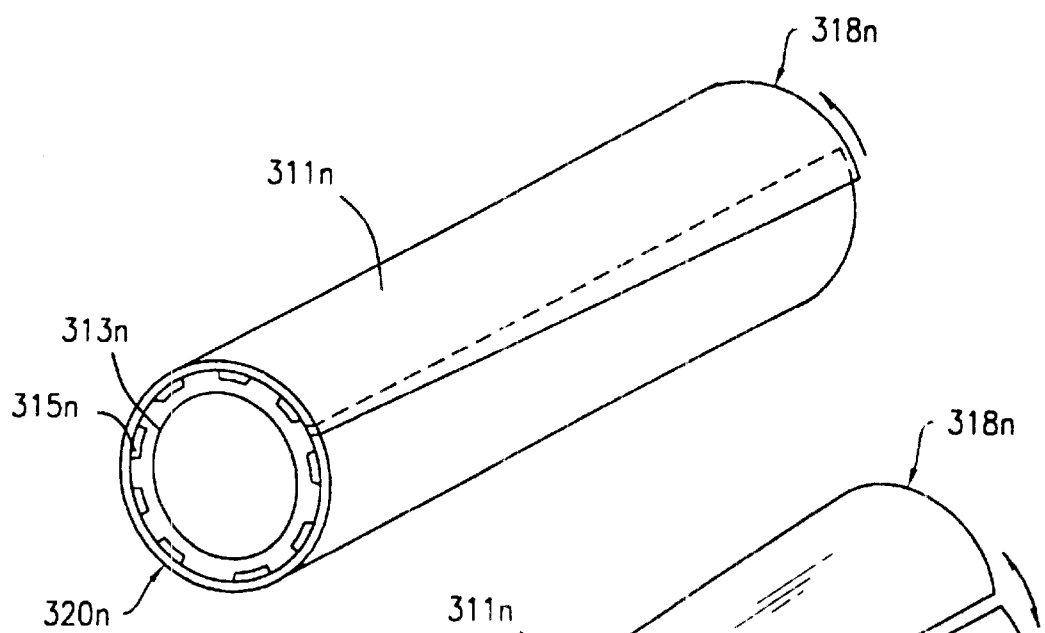
FIG. 6A
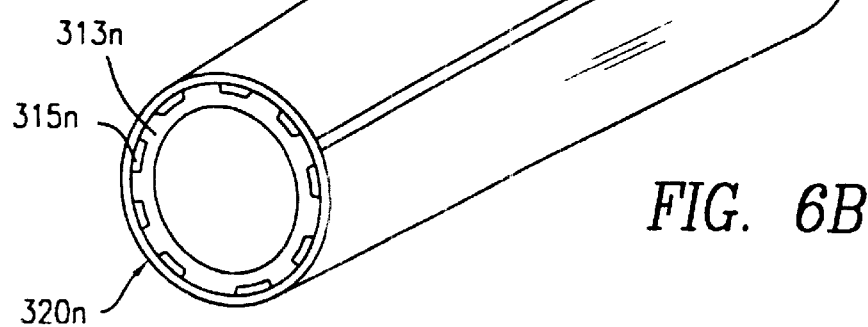
FIG. 6B
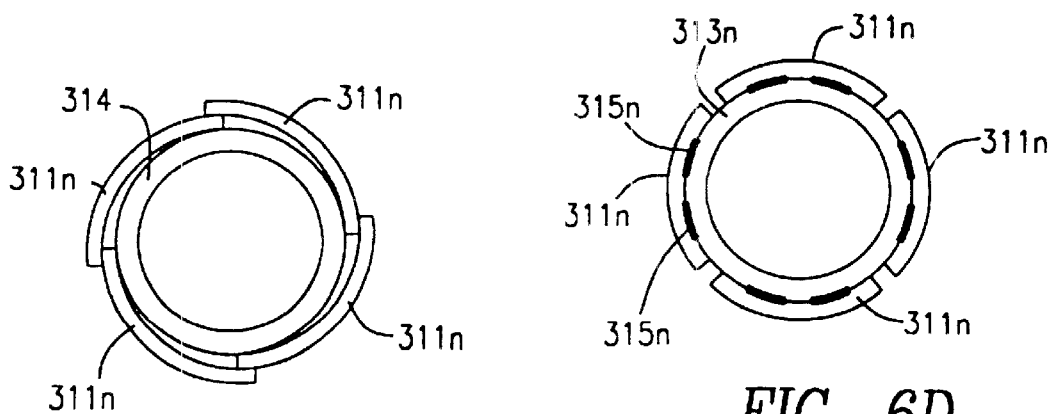
FIG. 6C
FIG. 6D

METHOD AND DEVICE TO ENHANCE RF ELECTRODE PERFORMANCE

FIELD OF THE INVENTION

The present invention relates to RF (radio frequency) electrode devices for use in the performance of RF thermal treatment and, more particularly, to such devices adapted for the percutaneous or luminal insertion into an affected tissue area of a patient to be treated.

BACKGROUND OF THE INVENTION

RF ablation (electrosurgery) is the application of RF energy from a source or device placed in tissue. Its use is to thermally treat malignant and nonmalignant tissue pathology and avoid or minimize a surgical procedure. The device may be placed percutaneously to assure minimally invasive techniques.

An RF electrode device is bipolar if it has both an active and a return electrode member (a negative (−) and a positive (+) electrode member) and if a return patch is not needed on the skin (as in electrosurgery). The RF signal is an alternating current at frequencies typically between 100 kHz and 2 MHz, optimally around 500 kHz. It will be understood that the positive (+) and negative (−) labels used herein are for descriptive purposes only. The active and return electrodes in the bipolar device could be swapped at a generator source with no change in performance. Unfortunately, the physics of bipolar designs limits their performance to small heated volumes due to the shape and proximity of the electrodes and the shape of the electric field. Due to the rapid falloff of an electric field that is produced by these RF electrode devices when in use, the area of treatment within a patient is limited.

Problems associated with previous RF electrode devices include the penetration and shape of the electric field being limited for these current RF electrode devices, as the heated volume within a patient cannot be increased without having to increase the number of RF electrode devices or having to increase the size of the RF electrode devices. If an increase in the number of RF electrode devices or in the size of the RF electrode devices is required, the RF ablation would be impractical, difficult to apply, and lose its percutaneous application.

Other RF electrode devices have tried to solve the foregoing problems by deploying needles in a fan-like branch array to spread out the conductive surfaces. The deployment of these RF electrode devices having a predetermined size and shape may depend on the tissue type of a patient, and the fan-like branch array could easily bend during deployment within the tissue of a patient. Current deployable electrodes may converge or diverge, which is not desirable in RF heating and may overheat when the conductive sources are close together and fail to interact when they are far apart.

Bipolar RF electrodes of various configurations, designs, structures and materials of construction are well known in the prior art, as shown in U.S. Pat. No. 6,066,139. The RF electrode device disclosed in this patent, however, suffers from one or both of the following shortcomings: (1) it does not produce a uniform RF thermal treatment field for treating the diseased tissue; and (2) the RF thermal treatment field is limited in size because of the structural arrangement of the negative (−) and positive (+) electrode members on a bipolar electrode catheter.

FIG. 1A depicts a prior art RF electrode device A used in the performance of RF ablation so as to treat an affected tissue area B of a patient. The RF electrode device A is powered by an RF energy source, such as an electrosurgical generator C. As shown in FIG. 1A, the RF electrode device A includes a catheter D having two spaced-apart, electrically conductive cylindrical bipolar electrode members, one being a negative electrode assembly E and the other being a positive electrode assembly F. The electrode assemblies E, F are made from a metal that has a high electrical conductivity ($\sigma$) value.

A negative electrical lead line G is connected to the negative electrode assembly E, while a positive electrical lead line H is connected to the positive electrode assembly F. Both electrical lead lines G, H are connected to the electrosurgical generator C, which supplies voltage to the electrode assemblies E, F, via the lead lines G, H, respectively. When voltage is supplied to the electrode assemblies, E, F, RF energy is emitted from the electrode assemblies E, F, to the surrounding tissue areas. The emitted RF energy will encounter resistance from the surrounding tissue areas. This resistance generates heat in the surrounding tissue areas. The heat is then transferred to more remote tissue areas through thermal conductivity.

With reference to FIG. 1B, the amount of heat generated in the surrounding tissue areas is delineated by a plurality of isotherms, each representing a temperature zone. As depicted in FIG. 1B, the location of the hottest temperature zone is adjacent to the center of the RF electrode device A. It would be desirable to manipulate the temperature distribution, such that the hottest temperature zone is distributed from the center of the RF electrode device A to the outer ends of the electrode assemblies E, F.

In the foregoing circumstances, there remains a need for an RF electrode device used to perform RF ablation that minimizes the RF electrode size that has to be inserted into the affected tissue of a patient. Further, the RF electrode device will have the ability to treat a pathologic region with a single insertion thereof into the affected tissue. Additionally, the RF electrode device will provide a voltage gradient along an electrode, thereby reshaping the electric field within the pathologic region so as to custom configure the thermal treatment zone.

Accordingly, it is an object of the present invention to provide an RF electrode that minimizes the size and shape of an electrode housing that has to be inserted into the affected or diseased tissue of a patient.

Another object of the present invention is to provide an RF electrode that is comparable in performance to that of a larger electrode.

Another object of the present invention is to provide an RF electrode that has the ability to treat a pathologic region with a single insertion thereof into the affected tissue.

Another object of the present invention is to provide an RF electrode that will generate a voltage gradient along the electrode so as to reshape the electric field within the pathologic region and to custom configure the thermal treatment zone.

Another object of the present invention is to provide an RF electrode that allows for the reshaping of the thermal field during treatment if the present heating field configuration is not optimally heating the pathologic region of the affected tissue being treated.

Another object of the present invention is to provide an RF electrode that includes the ability to reshape the electric field for different tissue types that have different electrical and thermal properties.

Another object of the present invention is to provide an RF electrode that has multiple bipolar segments so as to achieve higher levels of safety and eliminate the incidence of skin burns under a return electrode.

A further object of the present invention is to provide an RF electrode that has enhanced performance characteristics which can be mass produced in an automated and economical manner and is readily affordable by the practitioner.

SUMMARY OF THE INVENTION

In accordance with the present invention, a bipolar electrode instrument is provided for use in the performance of RF ablation electrosurgery. The bipolar electrode instrument includes an elongated catheter for insertion into an affected tissue to be treated within a patient, and at least one pair of spaced-apart bipolar electrode members, each of the electrode members being connected to the catheter. Means for applying voltage to each of the electrode members is also included. The bipolar electrode instrument further includes regulating means for regulating the amount of heat generated by each of the electrode members when voltage is applied thereto.

Other features and aspects of the present invention will become more fully apparent from the following detailed description of the preferred embodiments, the appended claims and the accompanying drawings.

BRIEF DESCRIPTION OF THE DRAWINGS

Further objects, features and advantages of the present invention will become apparent upon the consideration of the following detailed description of the various exemplary embodiments considered in conjunction with the accompanying drawings, in which:

FIG. 4A is a detailed perspective view, similar to that of FIG. 2A, of an RF electrode device constructed in accordance with a third exemplary embodiment of the present invention;

FIG. 4B is a chart depicting temperature zones generated by the RF electrode device of the third embodiment;

FIG. 6A is a close-up view of a negative electrode assembly of FIG. 5A in a closed position;

FIG. 6B is a view similar to that of FIG. 6A, except that the negative electrode assembly is in an open position;

FIG. 6C is a front view of the negative electrode assembly of FIG. 6A;

FIG. 6D is a back view of the negative electrode assembly of FIG. 6A;

DETAILED DESCRIPTION OF THE EXEMPLARY EMBODIMENTS

Figures 1A, 1B:
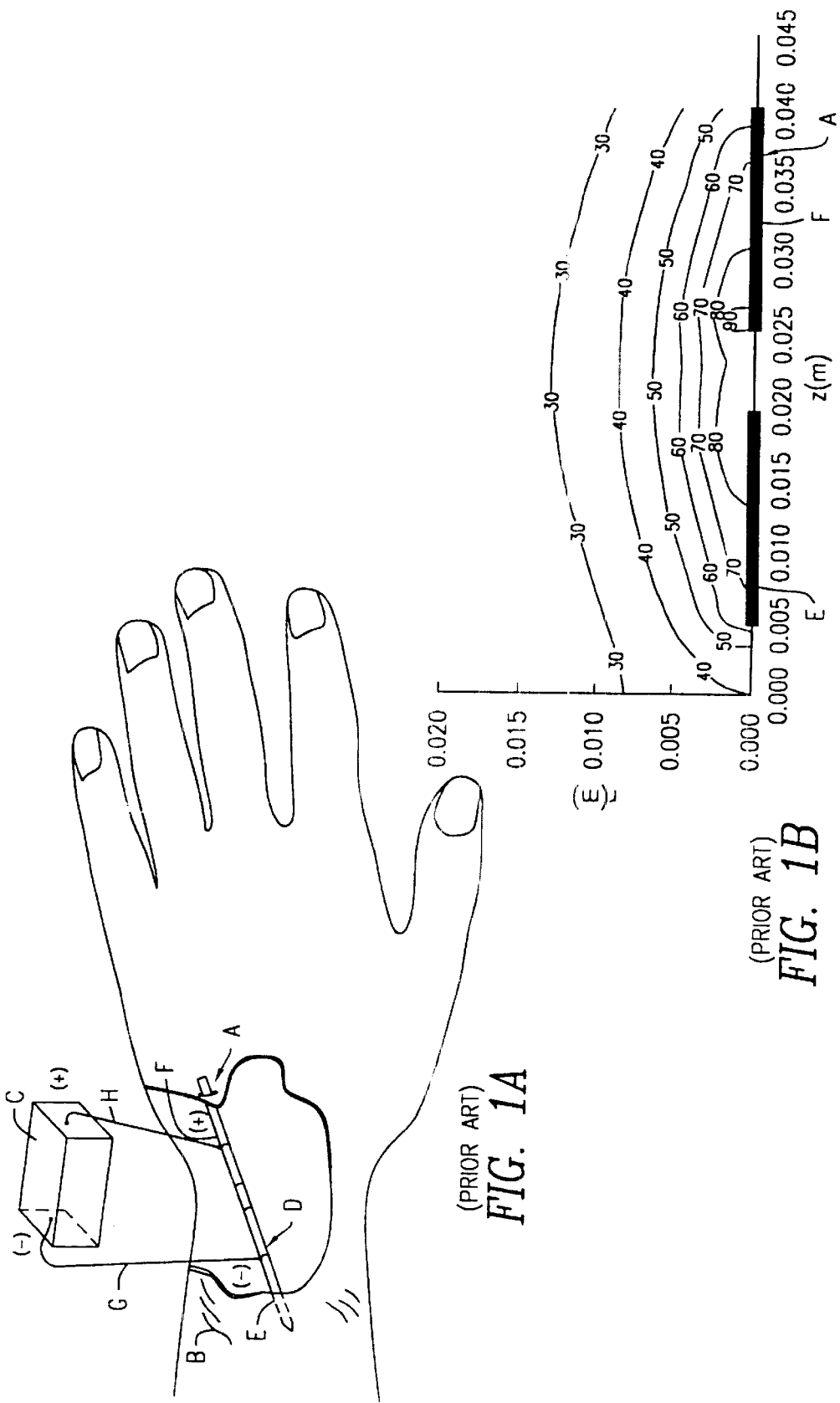
FIG. 1A is a schematic view of a conventional RF electrode device, the device being shown during use on a patient.
FIG. 1B is a chart depicting temperature zones generated by the conventional RF electrode device.
Figure 2A:
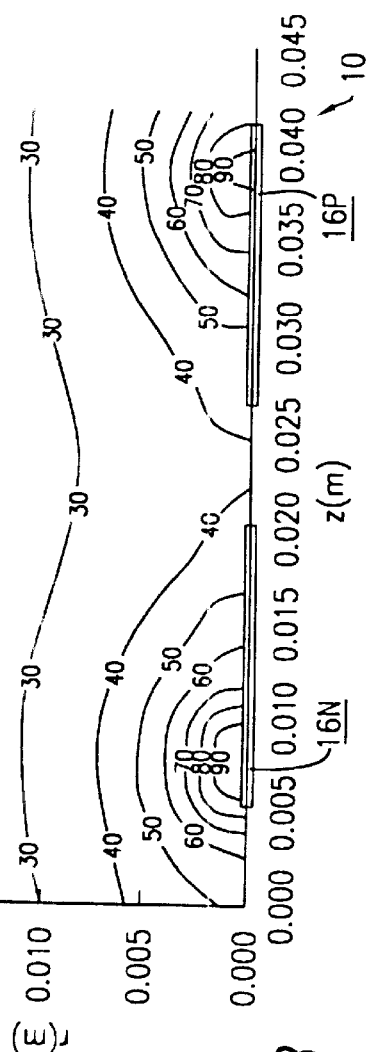
FIG. 2A is a detailed perspective view of an RF electrode device constructed in accordance with a first exemplary embodiment of the present invention.

With reference to FIG. 2A, an RF electrode device 10 is shown which is used in the performance of RF ablation so as to treat an affected tissue area of a patient. The RF electrode device 10 can be applied percutaneously to the affected tissue area. Alternatively, the RF electrode device 10 can be applied through a trocar surgical instrument, or can be applied through the lumen (passageway) within a tubular organ.

The RF electrode device 10 is powered by an RF energy source, such as an electrosurgical generator 12. As shown in FIG. 2A, the RF electrode device 10 includes a catheter 14 having two spaced-apart, electrically conductive cylindrical bipolar electrode members, one being a negative electrode assembly 16N and the other being a positive electrode assembly 16P. As used herein, the term "catheter" includes any electrode carrier. The electrode carrier can be rigid or flexible and can be polymer or metallic based with electrodes of conductive material mounted thereon. The electrode assemblies 16N, 16P are sized and shaped such that they fully circumscribe the catheter 14, and are attached thereto by attachment means such as adhesives, epoxies, laser bonding and ultrasonic welding.

The negative electrode assembly 16N includes an outer end 18n and an inner end 20n. Likewise, the positive electrode assembly 16P includes an outer end 18p and an inner end 20p. The electrode assemblies 16N, 16P are separated by a non-conductive catheter segment 22. A negative electrical lead line 24n is connected to the negative electrode assembly 16N at its outer end 18n, while a positive electrical lead line 24p is connected to the positive electrode assembly 16P at its outer end 18p. The electrical lead lines 24n, 24p are connected to the electrosurgical generator 12, which supplies voltage to the electrode assemblies 16N, 16P, via the electrical lead lines 24n, 24p, respectively.

The amount of voltage supplied to the electrode assemblies 16N, 16P is directly proportional to the amount of RF energy emitted therefrom. Also, the amount of RF energy emitted from the electrode assemblies 16N, 16P is directly proportional to the amount of heat generated in the surrounding tissue areas. The amount of heat generated from the electrode assemblies 16N, 16P is dependent on a patient's tissue type, pathology, tissue blood flow, physical properties of the tissue, the type of material used in each electrode assembly 16N, 16P, the type of material used for the catheter 14, the size of the RF electrode device 10, the amount of voltage applied to the electrode assemblies 16N, 16P, and the length of time for application procedure.

In this embodiment, each of the electrode assemblies 16N, 16P is made from a material which has a low electrical conductivity. An example of such a material is stainless steel, which has a resistivity value of 72. Because the electrode assemblies 16N, 16P are made from a material which has a low electrical conductivity and voltage is supplied to the electrode assemblies 16N, 16P at the outer ends 18n, 18p, respectively, there is a significant voltage decay starting from each of the outer ends 18n, 18p and terminating at the inner ends 20n, 20p. In such circumstances, when voltage is supplied to the electrode assemblies 16N, 16P, more energy will be emitted from the outer ends 18n, 18p thereof than the inner ends 20n, 20p thereof. The emitted RF energy will encounter resistance from the surrounding tissue areas. This resistance generates heat in the surrounding tissue areas. The heat is then transferred to more remote tissue areas through thermal conductivity. Because more RF energy is emitted from the outer ends 18n, 18p of the electrode assemblies 16N, 16P, than the inner ends 20n, 20p thereof, more heat will be generated in the tissue areas adjacent the outer ends 18n, 18p, than in the tissue areas adjacent the inner ends 20n, 20p.

Figure 2B:
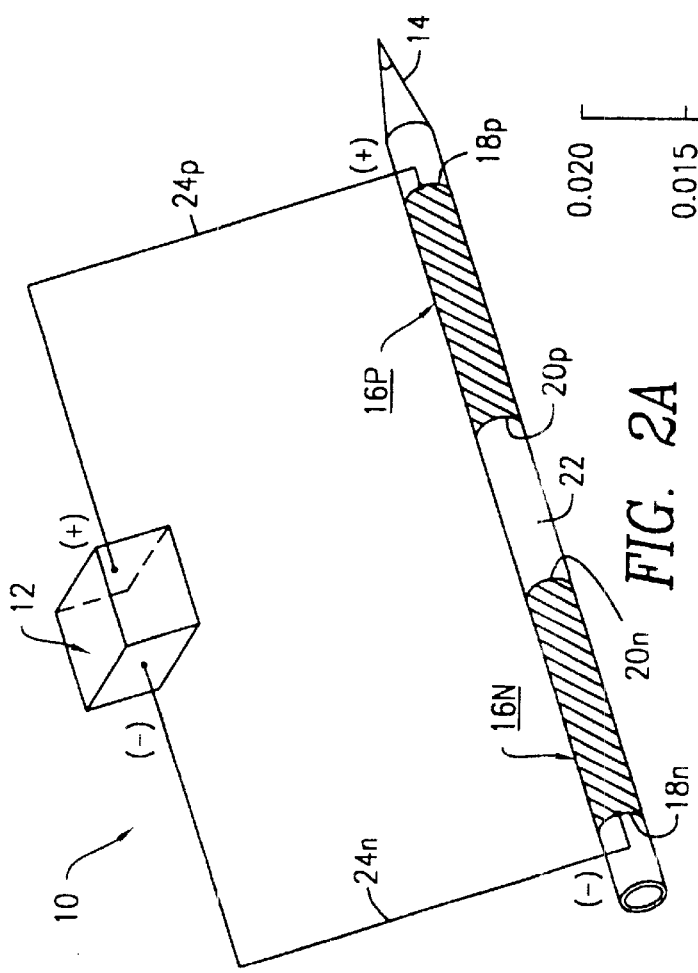
FIG. 2B is a chart depicting temperature zones generated by the RF electrode device of the first embodiment.

With reference to FIG. 2B, the amount of heat generated in the surrounding tissue areas is delineated by a plurality of isotherms, each representing a temperature zone. As depicted in FIG. 2B, the location of the hottest temperature zones is adjacent to the outer ends 18n, 18p of the electrode assemblies 16N, 16P. It should be appreciated that the RF electrode device 10 provides an advantage over the conventional RF electrode device discussed above. For instance, because the location of the hottest temperature zones is adjacent to the outer ends 18n, 18p of the electrode assemblies 16N, 16P, the heating volume is enlarged, and thus, the size of the surrounding tissue area being heated is increased.

The non-conductive catheter segment 22 has an optimal length which is determined based on the diameter of the catheter 14. If, on the one hand, the electrode assemblies 16N, 16P are spaced too far apart, this would result into two separate and discontinuous RF thermal treatment areas having a less effective total lesion area for treating the affected tissue. If, on the other hand, the electrode assemblies 16N, 16P are spaced too closely together, this would result in one smaller RF thermal treatment field having a minimally effective total lesion area for treating the affected tissue. For a 1 mm catheter diameter, the optimal length for the non-conductive catheter segment 22 is in a range of from about 1 mm to about 3 mm; and, for a 10 mm catheter diameter, the optimal length for the non-conductive catheter segment 22 is in a range of from about 10 mm to about 30 mm.

The catheter 14 can be made in varying lengths and diameters depending upon the type of RF ablation to be performed on a patient with regard to the affected tissue being treated. In general, the catheter 14 has a length in a range of from about 50 mm to about 150 mm, and a diameter in a range of from about 1 mm to about 10 mm. The catheter 14 can be made from various different materials such as teflon, urethane, nylon or other plastic polymers, and/or stainless steel. If the catheter 14 is made from stainless steel, a coating of a material that has a high dielectric constant, such as polyamide, is used on the outer wall surfaces thereof so as to provide sufficient electric insulating characteristics.

Typically, if the catheter 14 has a diameter of 1 mm, the voltage applied to each electrode assembly 16N, 16P is in a range of from about 10 volts to about 50 volts depending upon the tissue-type and area size of the affected tissue being treated. Alternatively, if the catheter 14 has a diameter of 10 mm, the voltage applied to each electrode assembly 16N, 16P is in a range of from about 20 volts to about 200 volts depending upon the tissue-type and area size of the affected tissue being treated.

Figures 3A, 3B:
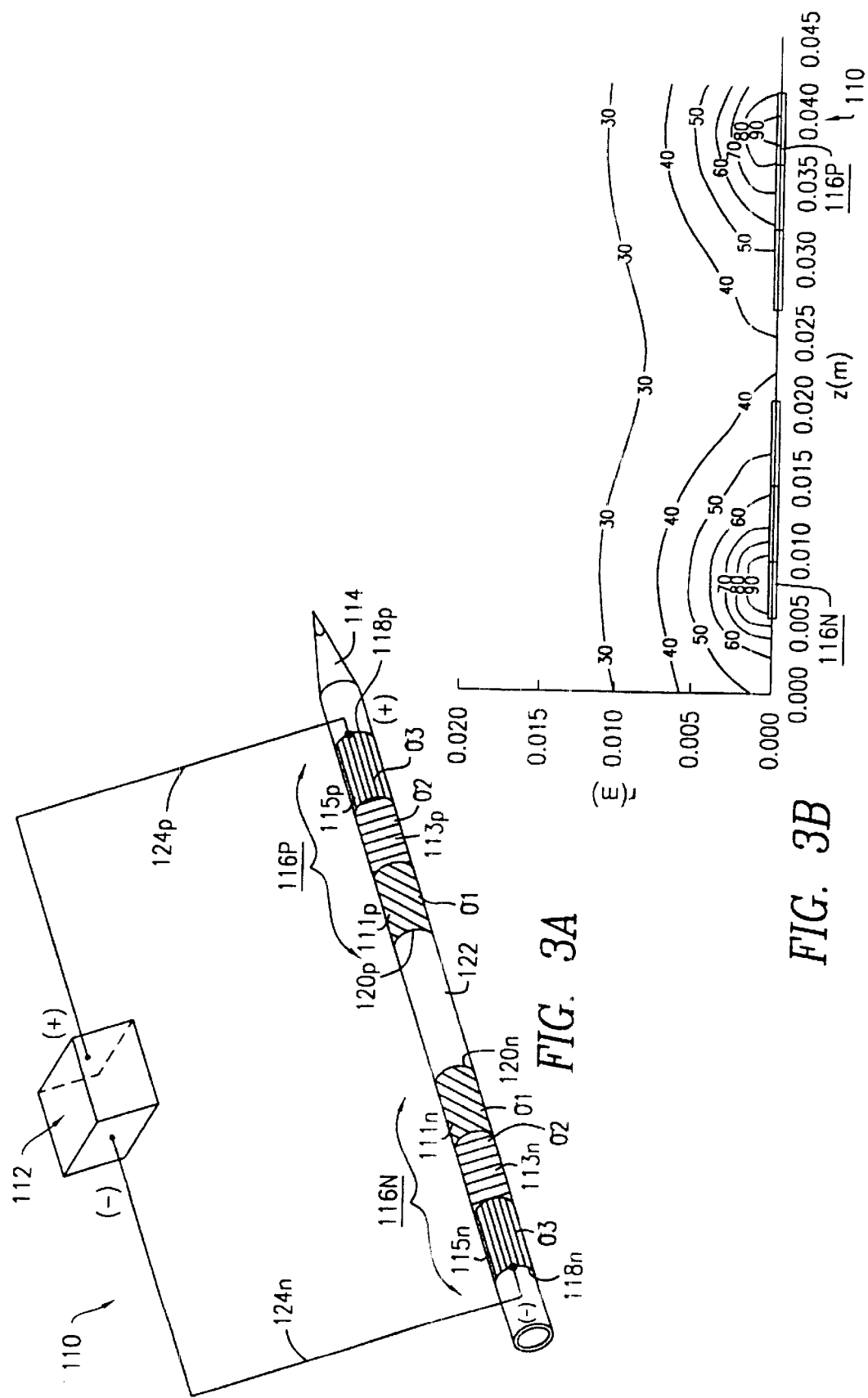
FIG. 3A is a detailed perspective view, similar to that of FIG. 2A, of an RF electrode device constructed in accordance with a second exemplary embodiment of the present invention.
FIG. 3B is a chart depicting temperature zones generated by the RF electrode device of the second embodiment.

A second exemplary embodiment of the present invention is illustrated in FIG. 3A. Elements illustrated in FIG. 3A which correspond to the elements described above with reference to FIG. 2A have been designated by corresponding reference numerals increased by one hundred. In addition, elements illustrated in FIG. 3A which do not correspond to the elements described above with reference to FIG. 2A have been designated by odd numbered reference numerals starting with reference number 111. The embodiment of FIG. 3A operates in the same manner as the embodiment of FIG. 2A, unless it is otherwise stated.

FIG. 3A shows an RF electrode device 110 powered by an electrosurgical generator 112. As shown in FIG. 3A, the RF electrode device 110 includes a catheter 114 having two spaced-apart, electrically conductive cylindrical bipolar electrode members, one being a negative electrode assembly 116N and the other being a positive electrode assembly 116P. A non-conductive catheter segment 122 separates the electrode assemblies 116N, 116P. The electrode assemblies 116N, 116P are sized and shaped such that they fully circumscribe the catheter 114.

The negative electrode assembly 116N includes an outer end 118n and an inner end 120n. A plurality of contiguous segmented ring-like sections 111n, 113n, and 115n extend seriating (i.e., in end-to-end fashion) between the inner end 120N and the outer end 118N. Likewise, the positive electrode assembly 116P includes an outer end 118p and an inner end 120p. A corresponding plurality of contiguous segmented ring-like sections 111p, 113p, and 115p extend seriating between the inner end 120P and the outer end 118P.

Each corresponding pair of segmented sections (i.e., the first pair which includes 111n and 111p, the second pair which includes 113n and 113p, and the third pair which includes 115n and 115p) can be made from different electrically conductive metals which are selected from a group including silver, gold, stainless steel, nitinol, and tantalum. Alternatively, each corresponding pair of segmented sections can be made from different electrically conductive polymers which are selected from a group including panipol™, baytron™, polyaniline, and ormecon™. Each of the foregoing metals and polymers has a different electrical conductivity ($\sigma$) value. Conductive metal materials have a conductivity range of from about 621,000 siemens per cm to about 10,000 siemens per cm, and conductive polymer materials have a conductivity range of from about 100 siemens per cm to about $10^{-12}$ siemens per cm.

The corresponding pair of segmented sections 111n and 111p are made from one of the foregoing metals or polymers which has an electrical conductivity value designated as $\sigma_1$. Further, the corresponding pair of segmented sections 113n and 113p are made from one of the foregoing metals or polymers which has an electrical conductivity value designated as $\sigma_2$. Likewise, the corresponding pair of segmented sections 115n and 115p are made from one of the foregoing metals or polymers which has an electrical conductivity value designated as $\sigma_3$. Each corresponding pair of segmented sections has a different electrical conductivity ($\sigma$) value, such that $\sigma_3 > \sigma_2 > \sigma_1$.

A negative electrical lead line 124n is connected to the segmented section 115n at the outer end 118n, while a positive electrical lead line 124p is connected to the segmented section 115p at the outer end 118p. Both electrical lead lines 124n, 124p are connected to the electrosurgical generator 112 which supplies voltage to the electrode assemblies 116N, 116P, via the electrode lead lines 124n, 124p, respectively.

The amount of RF energy emitted from each corresponding pair of segmented segments is directly proportional to their electrical conductivity value as well as to the amount of voltage that is supplied thereto. When voltage is supplied to the electrode assemblies 116N, 116P at the outer ends 118n, 118p, respectively, there will be a gradual voltage decay starting from each of the outer ends 118n, 118p and terminating at the inner ends 120n, 120p.

When voltage is supplied, the corresponding pair of segmented sections 115n, 115p generate the greatest amount of heat, because they are formed of a material that has the greatest electrical conductivity value ($\sigma_3$) and therefore, the least resistance. Also, the corresponding pair of segmented sections 115n, 115p generate the greatest amount of heat because the voltage is at its greatest value. The corresponding pair of segmented sections 113n, 113p generate less heat than that generated by the segmented sections 115n, 115p, because the segmented sections 115n, 115p are formed of a material that has an electrical conductivity value ($\sigma_2$) which is less than the electrical conductivity value ($\sigma_3$) of the segmented sections 115n, 115p. Further, the corresponding pair of segmented sections 111n, 111p generate the least amount of heat, because they are formed of a material that has the least electrical conductivity value ($\sigma_1$) and therefore, the greatest resistance.

With reference to FIG. 3B, the amount of heat generated in the surrounding tissue areas is delineated by a plurality of isotherms, each representing a temperature zone. As depicted in FIG. 3B, the location of the hottest temperature zones is adjacent to the outer ends 118n, 118p, and therefore, adjacent to the corresponding pair of segmented sections 115n, 115p. By varying the electrical conductivity value of each corresponding pair of segmented sections, the amount of heat generated by each corresponding pair of segmented sections can be regulated.

The negative and positive electrode assemblies 116N, 116P can vary in length and diameter depending upon the diameter of the catheter 114 used in a given RF ablation procedure. At a smaller catheter size diameter (1 mm), each segmented section has a length in a range of from about 1 mm to about 5 mm. The thickness of each segmented section is in a range of from about 10 mils to about 15 mils (0.25 mm to 0.375 mm). Each segmented section is swaged onto the catheter 114 by heating the segmented section and properly positioning the heated and expanded segmented section on the catheter 114. Then, each segmented section is allowed to cool on the catheter 114, thereby locking the segmented section firmly in place thereon. Each segmented section is so thin that it is almost flush with an outer wall surface of the catheter 114.

A third exemplary embodiment of the present invention is illustrated in FIG. 4A. Elements illustrated in FIG. 4A which correspond to the elements described above with reference to FIG. 2A have been designated by corresponding reference numerals increased by two hundred. In addition, elements illustrated in FIG. 4A which do not correspond to the elements described above with reference to FIG. 2A have been designated by odd numbered reference numerals starting with reference numeral 211. The embodiment of FIG. 4A operates in the same manner as the embodiment of FIG. 2A, unless it is otherwise stated.

FIG. 4A shows an RF electrode device 210 which includes a catheter 214 having two spaced-apart, electrically conductive cylindrical electrode members, one being a negative electrode assembly 216N and the other being a positive electrode assembly 216P. A non-conductive catheter segment 222 separates the electrode assemblies 216N, 216P. The electrode assemblies 216N, 216P are sized and shaped such that they fully circumscribe the catheter 214.

The negative electrode assembly 216N includes an outer end 218n and an inner end 220n. A plurality of non-contiguous segmented ring-like sections 211n, 213n, and 215n is included between the inner end 220n and the outer end 218n. In addition, a small interior non-conductive section 217n is located between the segmented sections 211n, 213n, and another small interior non-conductive section 219n is located between the segmented sections 213n, 215n. Likewise, the positive electrode assembly 216P includes an outer end 218p and an inner end 220p. A corresponding plurality of segmented ring-like sections 211p, 213p, and 215p are included between the inner end 220p and the outer end 218p. Further, a small interior non-conductive section 217p is located between the segmented sections 211p, 213p, and another small interior non-conductive section 219p is located between the segmented sections 213p, 215p.

Each of the segmented sections is made from the same material such that they have equivalent electrical conductivity values as further described below. Alternatively, each corresponding pair of the segmented sections can be made from different electrically conductive metals so that each pair of segmented sections has different electrical conductivity values.

Additionally, the segmented section 211n includes a negative electrical lead line 224an, the segmented section 213n includes a negative electrical lead line 224bn, and the segmented section 215n includes a negative electrical lead line 224cn. Similarly, the corresponding segmented section 211p includes a positive electrical lead line 224ap, the segmented section 213p includes a positive electrical lead line 224bp, and the segmented section 215p includes a positive electrical lead line 224cp. The foregoing lead lines are attached to an electrosurgical generator 212 for providing three different voltage levels $V_1$, $V_2$, and $V_3$ as shown in FIG. 4A, wherein $V_3 > V_2 > V_1$.

The aforementioned electrode configuration of the RF electrode device 210 creates a voltage distribution by varying the voltage ($V_1$, $V_2$ and $V_3$) that is applied to each corresponding pair of segmented sections (i.e., the first pair which includes 211n and 211p, the second pair which includes 213n and 213p, and the third pair which includes 215n and 215p). For example, the voltage ($V_3$) applied to the paired segmented sections 215n and 215p is about 50 volts, the voltage ($V_2$) applied to paired segmented sections 213n and 213p is about 20 volts, and the voltage ($V_1$) applied to paired segmented sections 211n and 211p is about 10 volts, thereby creating the aforementioned voltage distribution.

The amount of voltage supplied to each corresponding pair of segmented sections is directly proportional to the amount of RF energy emitted therefrom. Because the greatest amount of voltage is applied to the corresponding segmented sections 215n, 215p, they generate the greatest amount of heat. The corresponding segmented sections 213n, 213p generate less heat than that generated by the segmented sections 215n, 215p, because less voltage is applied thereto than that applied to the segmented sections 215n, 215p. Likewise, the corresponding segmented sections 211n, 211p generate the least amount of heat because the least amount of voltage is applied thereto.

With reference to FIG. 4B, the amount of heat generated in the surrounding tissue areas is delineated by a plurality of isotherms, each representing a temperature zone. As depicted in FIG. 4B, the location of the hottest temperature zones is adjacent to the outer ends 218n, 218p, and therefore, adjacent to the corresponding pair of segmented sections 215n, 215p. By varying the amount of voltage applied to each pair of segmented sections, the amount of heat generated by each pair of segmented sections can be regulated.

A fourth exemplary embodiment of the present invention is illustrated in FIGS. 5A–7B. Elements illustrated in FIGS. 5A–7B which correspond to the elements described above with reference to FIG. 2A have been designated by corresponding reference numerals increased by three hundred. In addition, elements illustrated in FIGS. 5A–7B which do not correspond to the elements described above with reference to FIG. 2A have been designated by odd numbered reference numerals starting with reference numeral 311. The embodiment of FIGS. 5A–7 operates in the same manner as the embodiment of FIG. 2A, unless it is otherwise stated.

Figure 5A:
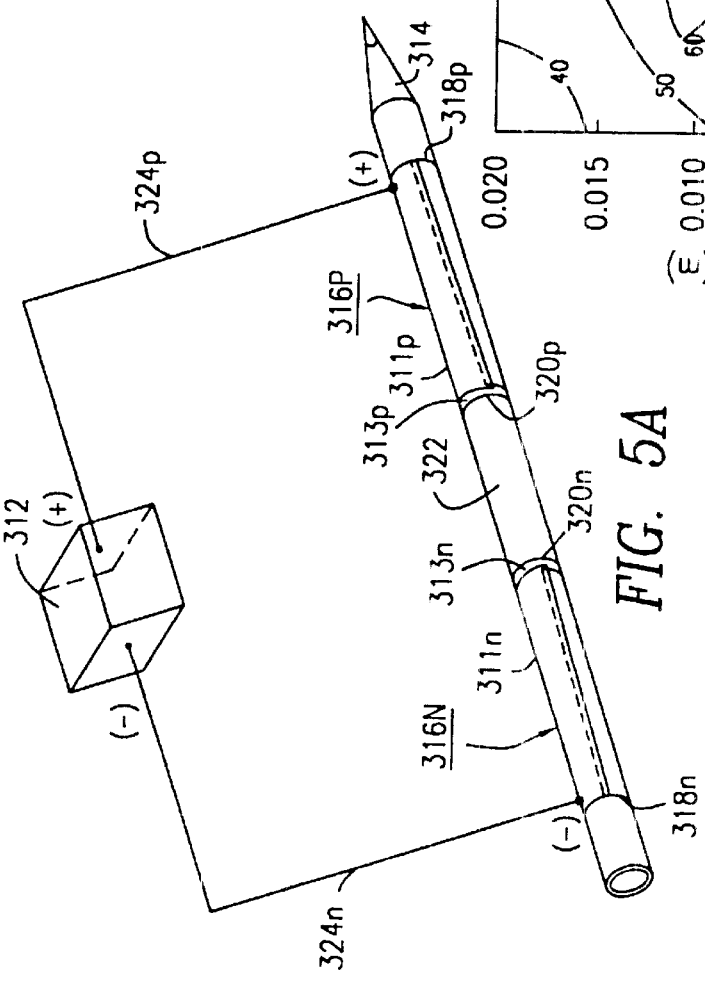
FIG. 5A is a detailed perspective view, similar to that of FIG. 2, of an RF electrode device constructed in accordance with a fourth exemplary embodiment of the present invention, the device being shown in a closed position.

FIG. 5A shows an RF electrode device 310 powered by an electrosurgical generator 312. As shown in FIG. 5A, the RF electrode device 310 includes a catheter 314 having two spaced-apart, electrically conductive cylindrical electrode members, one being a negative electrode assembly 316N and the other being a positive electrode assembly 316P. The electrode assemblies 316N, 316P are sized and shaped such that they fully circumscribe the catheter 314.

The negative electrode assembly 316N includes an outer end 318n and an inner end 320n. Likewise, the positive electrode assembly 316P includes an outer end 318p and an inner end 320p. The electrode assemblies 316N, 316P are separated by a non-conductive catheter segment 322. A negative electrical lead line 324n is connected to the negative electrode assembly 316N at its outer end 318n, while a positive electrical lead line 324p is connected to the positive electrode assembly 316p at its outer end 318p. The electrical lead lines 324n, 324p are connected to the electrosurgical generator 312, which supplies voltage to the electrode assemblies 316N, 316P, via the electrical lead lines 324n, 324p, respectively.

Figure 5B:
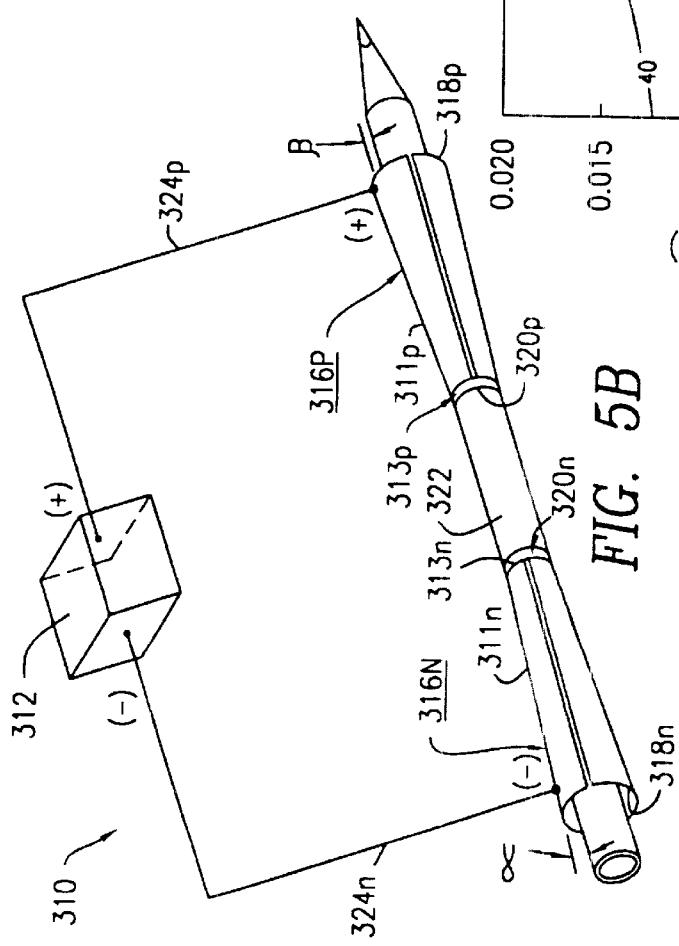
FIG. 5B is a view similar to that of FIG. 5A, except that the RF electrode device is in an open position.

The negative electrode assembly 316N can be deployed to an open (i.e., expanded) position as shown in FIG. 5B or to a closed (i.e., contracted) position as shown in FIG. 5A by mechanical means, such as by a rod-struts arrangement. Also, the negative electrode assembly 316N includes four interleaved metal strips 311n and a collar 313n, at its inner end 320n, which is sized and shaped to hold in place the interleaved metal strips 311n and which functions as an anchor. As shown in FIG. 6D, the four interleaved metal strips 311n and the collar 313n are attached to each other via hinges 315n, such that the interleaved metal strips 311n can pivot about the collar 313n in a direction away or toward the catheter 314. When the interleaved metal strips 313n pivot about the collar 315n in a direction away from the catheter 314, the outer end 318n of the negative electrode assembly 316N expands radially outward. This places the negative electrode assembly 316N in the open position as shown in FIG. 6B. In the open position, a gap exists between each of the interleaved metal strips 311n as shown in FIG. 6B. When the negative electrode assembly 316N is in its open position, the interleaved metal strips 311n is at an angle of deflection (α) in a range of from about 15° to about 45° relative to the collar 313n as shown in FIG. 5B. Likewise, when the interleaved metal strips 313n pivot about the collar 315n in a direction toward the catheter 314, the outer end 318n of the negative electrode assembly 316N contracts radially inward. This places the negative electrode assembly 316n in the closed position as shown in FIG. 6A. In the closed position, the interleaved metal strips 313n overlap each other as shown in FIGS. 6A and 6C.

The positive electrode assembly 316P can be deployed to an open (i.e., expanded) position as shown in FIG. 5B or to a closed (i.e., contracted) position as shown in FIG. 5A by mechanical means, such as by a rod-struts arrangement. Also, the positive electrode assembly 316P includes four interleaved metal strips 311p and a collar 313p, at its inner end 320p, which is sized and shaped to hold in place the interleaved metal strips 311p and which functions as an anchor. The four interleaved metal strips 311p and the collar 313p are attached to each other via hinges (not shown), such that the interleaved metal strips 311p can pivot about the collar 313p in a direction away or toward the catheter 314. When the interleaved metal strips 311p pivot about the collar 313p in a direction away from the catheter 314, the outer end 318p of the positive electrode assembly 316P expands radially outward. This places the positive electrode assembly 316P in the open position as shown in FIG. 5B. In the open position, a gap exists between each of the interleaved metal strips 311p as shown in FIG. 5B. When the positive electrode assembly 316P is in its open position, the interleaved metal strips 311p is at an angle of deflection (β) in a range of from about 15° to about 45° relative to the collar 313p as shown in FIG. 5B. Likewise, when the interleaved metal strips 311p pivot about the collar 313p in a direction toward the catheter 314, the outer end 318p of the positive electrode assembly 316P contracts radially inward. This places the positive electrode assembly 316p in the closed position as shown in FIG. 5A.

Each of the interleaved metal strips 311n, 311p is made of a high level electrically conductive metallic material (e.g., silver which has a conductivity value of approximately 621,000 siemens per cm). The surface area of each electrode assembly 316N, 316P is directional proportional to the amount of RF energy emitted therefrom. In the open positions, the surface area of the electrode assemblies 316N, 316P increases and is directly proportional to the angle of deflection of the interleaved metal strips 311n, 311p relative to the collars 313n, 313p, respectively.

Figure 7B:
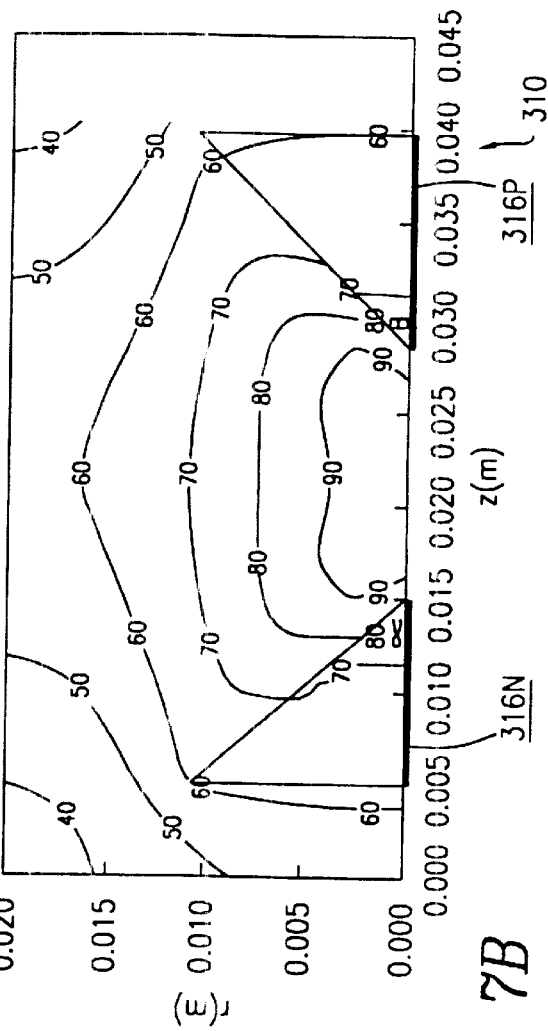
FIG. 7B is a view similar to that of FIG. 7A, except that the RF electrode device is in a fully open position.
Figure 7A:
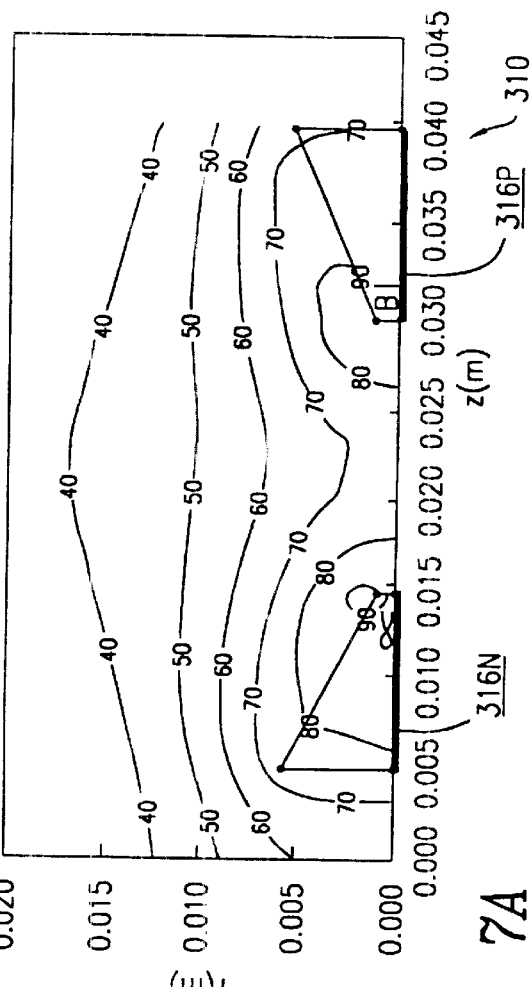
FIG. 7A is a chart depicting temperature zones generated by the RF electrode device of the fourth embodiment when the RF electrode device is in a partially open position.

With reference to FIGS. 7A and 7B, the amount of heat generated in the surrounding tissue areas is delineated by a plurality of isotherms, each representing a temperature zone. FIG. 7A depicts the location of the temperature zones when the angle of deflection of the interleaved metal strips 311n, 311p is about 30 degrees relative to the collars 313n, 313p. When the angle of deflection increases to about 45 degrees between the interleaved metal strips 311n, 311p and the collars 313n, 313p, respectively, the size of the hottest temperature zones expands as depicted in FIG. 7B. By varying the surface area of the electrode assemblies 316N, 316P, the amount of heat generated by each of the electrode assemblies 316N, 316P can be regulated.

It should be understood that the embodiments described herein are merely exemplary and that a person skilled in the art may make many variations and modifications without departing from the spirit and scope of the invention as defined in the appended claims. Accordingly, all such variations and modifications are intended to be included within the scope of the invention as defined in the appended claims.

What is claimed is:

1. A bipolar electrode instrument for use in the performance of RF ablation electrosurgery, comprising an elongated catheter for insertion into an affected tissue to be treated within a patient; at least one pair of spaced-apart bipolar electrode members, each of said electrode members being connected to said catheter; means for applying voltage to each of said electrode members; and means for regulating the amount of heat generated by each of said electrode members when voltage is applied thereto, wherein one of said electrode members is a negative electrode assembly and the other of said electrode members is a positive electrode assembly, said negative electrode assembly including a negative outer end and a negative inner end, said positive electrode assembly including a positive outer end and a positive inner end, said negative inner end being proximate to said positive inner end, said negative outer end being remote from said positive inner end, and said positive outer end being remote from said negative inner end, and wherein said means for applying voltage includes a negative electrical line connected to said negative outer end of said negative electrode assembly, and a positive electrical line connected to said positive outer end of said positive electrode assembly, and an RF energy source connected to said negative electrical line and to said positive electrical line.

2. The bipolar electrode instrument of claim 1, wherein said negative electrode assembly and said positive electrode assembly are made from a material which has a low electrical conductivity value.

3. The bipolar electrode instrument of claim 2, wherein said negative outer end and said negative inner end of said negative electrode assembly are sized and shaped to emit RF energy, said negative outer end of said negative electrode assembly emitting more RF energy than that emitted by said negative inner end of said negative electrode assembly when voltage is applied to said negative electrode assembly; and wherein said positive outer end and said positive inner end of said positive electrode assembly are sized and shaped to emit RF energy, said positive outer end of said positive electrode assembly emitting more RF energy than that emitted by said positive inner end of said positive electrode assembly when voltage is applied to said positive electrode assembly.

4. The bipolar electrode instrument of claim 1, wherein said negative electrode assembly includes a plurality of contiguous segmented sections and said positive electrode assembly includes a plurality of contiguous segmented sections.

5. The bipolar electrode instrument of claim 4, wherein said contiguous segmented sections of said negative electrode assembly include a first section, a second section, and a third section; and wherein said contiguous segmented sections of said positive electrode assembly include a first section, a second section, and a third section.

6. The bipolar electrode instrument of claim 1, wherein said negative electrode assembly includes a plurality of segmented sections, each adjacent pair of which is separated by a nonconductive section; and wherein said positive electrode assembly includes a plurality of segmented sections, each adjacent pair of which is separated by a nonconductive section.

7. The bipolar electrode instrument of claim 6, wherein said means for applying voltage includes a plurality of negative electrical lines, each of said negative electrical lines being connected to a corresponding one of said segmented sections of said negative electrode assembly, a plurality of positive electrical lines, each of said positive electrical lines being connected to a corresponding one of said segmented sections of said positive electrode assembly, and an RF energy source connected to each of said negative electrical lines and to each of said positive electrical lines.

8. The bipolar electrode instrument of claim 7, wherein said segmented sections of said negative electrode assembly include a first section, a second section, and a third section; and wherein said segmented sections of said positive electrode assembly include a first section, a second section, and a third section.

9. A bipolar electrode instrument for use in the performance of RF ablation electrosurgery, comprising an elonoated catheter for insertion into an affected tissue to be treated within a patient; at least one pair of spaced-apart bipolar electrode members, each of said electrode members being connected to said catheter; means for applying voltage to each of said electrode members; and means for regulating the amount of heat generated by each of said electrode members when voltage is applied thereto, wherein one of said electrode members is a negative electrode assembly and the other of said electrode members is a positive electrode assembly, said negative electrode assembly including a plurality of contiguous segmented sections and said positive electrode assembly including a plurality of contiguous segmented sections, said contiguous segmented sections of said negative electrode assembly including a first section, a second section, and a third section, said contiguous segmented sections of said positive electrode assembly including a first section, a second section, and a third section, said first section of said negative electrode assembly and said first section of said positive electrode assembly being made from a material which has a first electrical conductivity value, said second section of said negative electrode assembly and said second section of said positive electrode assembly being made from a material which has a second electrical conductivity value and, said third section of said negative electrode assembly and said third section of said positive electrode assembly being made from a material which has a third electrical conductivity value, said third electrical conductivity value being greater than said second electrical conductivity value and said second electrical conductivity value being greater than said first electrical conductivity value.

10. The bipolar electrode instrument of claim 9, wherein said negative electrode assembly includes a negative outer end and a negative inner end; wherein said positive electrode assembly includes a positive outer end and a positive inner end; and wherein said means for applying voltage includes a negative electrical line connected to said negative outer end of said negative electrode assembly, and a positive electrical line connected to said positive outer end of said positive electrode assembly, and an RF energy source connected to said negative electrical line and to said positive electrical line, said third section of said negative electrode assembly forming said negative outer end of said negative electrode assembly, said third section of said positive electrode assembly forming said positive outer end of said positive electrode assembly, said first section of said negative electrode assembly forming said negative inner end of said negative electrode assembly, and said first section of said positive electrode assembly forming said positive inner end of said positive electrode assembly.

11. The bipolar electrode instrument of claim 10, wherein said first section, said second section, and said third section of said negative electrode assembly are sized and shaped to emit RF energy, said third section of said negative electrode assembly emitting more RF energy than that emitted by said second section of said negative electrode assembly when voltage is applied to said negative electrode assembly, and said second section of said negative electrode assembly emitting more RF energy than that emitted by said first section of said negative electrode assembly when voltage is applied to said negative electrode assembly; and wherein said first section, said second section, and said third section of said positive electrode assembly are sized and shaped to emit RF energy, said third section of said positive electrode assembly emitting more RF energy than that emitted by said second section of said positive electrode assembly when voltage is applied to said positive electrode assembly, and said second section of said positive electrode assembly emitting more RF energy than that emitted by said first section of said positive electrode assembly when voltage is applied to said positive electrode assembly.

12. A bipolar electrode instrument for use in the performance of RF ablation electrosurgery, comprising an elongated catheter for insertion into an affected tissue to be treated within a patient; at least one pair of spaced-apart bipolar electrode members, each of said electrode members being connected to said catheter; means for applying voltage to each of said electrode members; and means for regulating the amount of heat generated by each of said electrode members when voltage is applied thereto, wherein one of said electrode members is a negative electrode assembly and the other of said electrode members is a positive electrode assembly, said negative electrode assembly including a plurality of segmented sections, each adjacent pair of which is separated by a nonconductive section, said positive electrode assembly including a plurality of segmented sections, each adjacent pair of which is separated by a nonconductive section, said means for applying voltage including a plurality of negative electrical lines, each of said negative electrical lines being connected to a corresponding one of said segmented sections of said negative electrode assembly, a plurality of positive electrical lines, each of said positive electrical lines being connected to a corresponding one of said segmented sections of said positive electrode assembly, and an RF energy source connected to each of said negative electrical lines and to each of said positive electrical lines, said segmented sections of said negative electrode assembly including a first section, a second section, and a third section, said segmented sections of said positive electrode assembly including a first section, a second section, and a third section, said negative electrode assembly including a negative outer end and a negative inner end, said third section of said negative electrode assembly forming said negative outer end of said negative electrode assembly, and said first section of said negative electrode assembly forming said negative inner end of said negative electrode assembly and, said positive electrode assembly including a positive outer end and a positive inner end, said third section of said positive electrode assembly forming said positive outer end of said positive electrode assembly, and said first section of said positive electrode assembly forming said positive inner end of said positive electrode assembly.

13. The bipolar electrode instrument of claim 12, wherein said first section of said negative electrode assembly and said first section of said positive electrode assembly are subjected to a first voltage; wherein said second section of said negative electrode assembly and said second section of said positive electrode assembly are subjected to a second voltage; and wherein said third section of said negative electrode assembly and said third section of said positive electrode assembly are subjected to a third voltage, said third voltage being greater than said second voltage and said second voltage being greater than said first voltage.

14. The bipolar electrode instrument of claim 13, wherein said first section, said second section, and said third section of said negative electrode assembly are sized and shaped to emit RF energy, said third section of said negative electrode assembly emitting more RF energy than that emitted by said second section of said negative electrode assembly when voltage is applied thereto, and said second section of said negative electrode assembly emitting more RF energy than that emitted by said first section of said negative electrode assembly when voltage is applied thereto; and wherein said first section, said second section, and said third section of said positive electrode assembly are sized and shaped to emit RF energy, said third section of said positive electrode assembly emitting more RF energy than that emitted by said second section of said positive electrode assembly when voltage is applied thereto, and said second section of said positive electrode assembly emitting more RF energy than that emitted by said first section of said positive electrode assembly when voltage is applied thereto.

15. A bipolar electrode instrument for use in the performance of RF ablation electrosurgery, comprising an elongated catheter for insertion into an affected tissue to be treated within a patient; at least one pair of spaced-apart bipolar electrode members, each of said electrode members being connected to said catheter; means for applying voltage to each of said electrode members; and means for regulating the amount of heat generated by each of said electrode members when voltage is applied thereto, wherein one of said electrode members is a negative electrode assembly and the other of said electrode members is a positive electrode assembly, said negative electrode assembly including a negative outer end and a negative inner end, said positive electrode assembly including a positive outer end and a positive inner end, said means for applying voltage including a negative electrical line connected to said negative outer end, and a positive electrical line connected to said positive outer end, and an RF energy source connected to said negative electrical line and to said positive electrical line, said negative electrode assembly including a first plurality of electrically conductive strips arranged in a radial array about one end of said catheter, said first plurality of electrically conductive strips being sized and shaped to move relative to said catheter such that said first plurality of electrically conductive strips is movable between a contracted position, in which said first plurality of electrically conductive strips is positioned adjacent to said catheter, and an expanded position, in which said first plurality of electrically conductive strips is positioned remote from said catheter and, said positive electrode assembly including a second plurality of electrically conductive strips arranged in a radial array about an opposite end of said catheter, said second plurality of electrically conductive strips being sized and shaped to move relative to said catheter such that said second plurality of electrically conductive strips is movable between a contracted position, in which said second plurality of electrically conductive strips is positioned adjacent to said catheter, and an expanded position, in which said second plurality of electrically conductive strips is positioned remote from said catheter.

16. The bipolar electrode instrument of claim 15, wherein said first plurality of electrically conductive strips forms a first angle with said catheter when said first plurality of electrically conductive strips is in its said expanded position; and wherein said second plurality of electrically conductive strips forms a second angle with said catheter when said second plurality of electrically conductive strips is in its said expanded position.

17. The bipolar electrode instrument of claim 16, wherein said negative electrode assembly and said positive electrode assembly are sized and shaped to emit RF energy, the amount of RF energy emitted by said negative electrode assembly being dependent on said first angle and the amount of RF energy emitted by said positive electrode assembly being dependent on said second angle.

* * * * *